(12) United States Patent
Chua et al.

(10) Patent No.: US 8,541,000 B2
(45) Date of Patent: Sep. 24, 2013

(54) VARIANT OF MITE ALLERGEN AND USES THEREOF

(75) Inventors: Kaw Yan Chua, Kulai (MY); Keh-Liang Lin, Taichung (TW); I-Chun Kuo, Taoyuan (TW); Chiung-Hui Huang, Hualien (TW)

(73) Assignee: Kaw Yan Chua, Johor (MY)

( * ) Notice: Subject to any disclaimer, the term of this patent is extended or adjusted under 35 U.S.C. 154(b) by 0 days.

(21) Appl. No.: 13/142,914

(22) PCT Filed: Dec. 30, 2008

(86) PCT No.: PCT/IB2008/003643
§ 371 (c)(1),
(2), (4) Date: Aug. 25, 2011

(87) PCT Pub. No.: WO2010/076583
PCT Pub. Date: Jul. 8, 2010

(65) Prior Publication Data
US 2011/0318274 A1    Dec. 29, 2011

(51) Int. Cl.
*A61K 39/00* (2006.01)
*A61K 39/35* (2006.01)
*A61K 39/36* (2006.01)
*C07K 1/00* (2006.01)
*C07K 14/00* (2006.01)
*C07K 17/00* (2006.01)

(52) U.S. Cl.
USPC ............. 424/185.1; 424/275.1; 530/350

(58) Field of Classification Search
None
See application file for complete search history.

(56) References Cited

FOREIGN PATENT DOCUMENTS
WO    WO 2007/140505 A2 * 12/2007
WO    2010/076583 A1    7/2010

OTHER PUBLICATIONS

Kuby et al. 'Immunology.' Fourth Edition, Chapter 18: 449-465, 2000.*
Mukherjee et al. 'Allergic Asthma: Influence of Genetic and Environmental Factors.' The Journal of Biological Chemistry vol. 286(38):32883-32889, 2011'.*
Kurucz et al. 'Current Animal Models of Bronchial Asthma.' Curr. Pharm. Des. 12:3175-3194, 2006.*
PCT International Search Report dated May 19, 2009 for PCT/IB2008/003643, which is a corresponding PCT application.
PCT Written Opinion of the International Search Report dated May 19, 2009 for PCT/IB2008/003643, which is a corresponding PCT application.

* cited by examiner

*Primary Examiner* — Nora Rooney
(74) *Attorney, Agent, or Firm* — WPAT, P.C.; Anthony King (57) ABSTRACT

The present invention relates to a new variant of the group 2 allergen from the house dust mite *Dermatophagoides pteronyssinus*, named Der p 2 variant, and uses thereof. The new variant exhibits cDNA and protein sequence diversity from other known Der p 2 variants.

2 Claims, 6 Drawing Sheets

```
                                                             cacaaatt    8 cttctttcttccttactactgatcattaatctgaaaacaaaaccaaacaaaccattcaaa   68

-17                                                           -1 +1
         atgatgtacaaaattttgtgtctttcattgttggtcgcagccgttgctgctgatcaagtc  128
           M  M  Y  K  I  L  C  L  S  L  L  V  A  A  V  A  A  D  Q  V    3 gatgtcaaagattgtgccaatcatgaaatcaaaaaagttttggtaccaggatgccatggt  188
           D  V  K  D  C  A  N  H  E  I  K  K  V  L  V  P  G  C  H  G   23

Tcagaatcatgtatcattcatcgtggtaaaccattccaattggaagccgttttcgaagcc  248
           S  E  S  C  I  I  H  R  G  K  P  F  Q  L  E  A  V  F  E  A   43 aaccaaaactcaaaaaccgctaaaattgaaatcaaagcttcaatcgatggtttagaagtt  308
           N  Q  N  S  K  T  A  K  I  E  I  K  A  S  I  D  G  L  E  V   63 gatgttcccggtatcgatccaaatgcatgccattatatgaaatgtccattggttaaagga  368
           D  V  P  G  I  D  P  N  A  C  H  Y  M  K  C  P  L  V  K  G   83 caacaatatgatattaaatatacatggaatgttccgaaaattgcaccaaaatctgaaaat  428
           Q  Q  Y  D  I  K  Y  T  W  N  V  P  K  I  A  P  K  S  E  N  103 gttgtcgtcactgttaaagttatgggtgataatggtgttttggcctgtgctattgctact  488
           V  V  V  T  V  K  V  M  G  D  N  G  V  L  A  C  A  I  A  T  123 catgctaaaatccgcgattaaattcagcaaacaaacaaaatttattgattttgtaatcaa  548
           H  A  K  I  R  D  -                                          129 atcaattgatttctttccaaaaaataaaaataagggaattc                       591
```

Figure 1

```
                                                           cacaaatt    8 cttctttcttccttactactgatcattaatctgaaaacaaaaccaaacaaaccattcaaa          68

-17                                                     -1 +1
atgatgtacaaaattttgtgtctttcattgttggtcgcagccgttgctcgtgatcaagtc         128
 M  M  Y  K  I  L  C  L  S  L  L  V  A  A  V  A  R  D  Q  V            3 gatgtcaaagattgtgccaatcatgaaatcaaaaaagttttggtaccaggatgccatggt         188
 D  V  K  D  C  A  N  H  E  I  K  K  V  L  V  P  G  C  H  G           23 tcagaaccatgtatcattcatcgtggtaaaccattccaattggaagccgttttcgaagcc         248
 S  E  P  C  I  I  H  R  G  K  P  F  Q  L  E  A  V  F  E  A           43 aaccaaaacacaaaaacggctaaaattgaaatcaaagcctcaatcgatggtttagaagtt         308
 N  Q  N  T  K  T  A  K  I  E  I  K  A  S  I  D  G  L  E  V           63 gatgttcccggtatcgatccaaatgcatgccattacatgaaatgcccattggttaaagga         368
 D  V  P  G  I  D  P  N  A  C  H  Y  M  K  C  P  L  V  K  G           83 caacaatatgatattaaatatacatggaatgttccgaaaattgcaccaaaatctgaaaat         428
 Q  Q  Y  D  I  K  Y  T  W  N  V  P  K  I  A  P  K  S  E  N          103 gttgtcgtcactgttaaagttatgggtgatgatggtgttttggcctgtgctattgctact         488
 V  V  V  T  V  K  V  M  G  D  D  G  V  L  A  C  A  I  A  T          123 catgctaaaatccgcgattaaatcaaacaaaatttattgattttgtaatcacaaatgatt         548
 H  A  K  I  R  D  -                                                 129 gattttctttccaaaaaaaaaataaataaaattttgggaattc                          591
```

Figure 2

```
Der p 2 variant T   CACAAATTCTTCTTTCTTCCTTACTACTGATCATTAATCTGAAAACAAAACCAAACAAAC  60
Der p 2.0101        ............................................................  60

Ala
Der p 2 variant T   CATTCAAAATGATGTACAAAATTTTGTGTCTTTCATTGTTGGTCGCAGCCGTTGCTGCTG  120
Der p 2.0101        ..........................................................CG..  120
                                                                       Arg Der p 2 variant T   ATCAAGTCGATGTCAAAGATTGTGCCAATCATGAAATCAAAAAAGTTTTGGTACCAGGAT  180
Der p 2.0101        ............................................................  180

Ser
Der p 2 variant T   GCCATGGTTCAGAATCATGTATCATTCATCGTGGTAAACCATTCCAATTGGAAGCCGTTT  240
Der p 2.0101        .............C..............................................  240
                             Pro
                             Ser
Der p 2 variant T   TCGAAGCCAACCAAAACTCAAAAACCGCTAAAATTGAAATCAAAGCTTCAATCGATGGTT  300
Der p 2.0101        .............A.......G............................C........  300
                                    Thr Der p 2 variant T   TAGAAGTTGATGTTCCCGGTATCGATCCAAATGCATGCCATTATATGAAATGTCCATTGG  360
Der p 2.0101        ..............................C........C...................  360

Der p 2 variant T   TTAAAGGACAACAATATGATATTAAATATACATGGAATGTTCCGAAAATTGCACCAAAAT  420
Der p 2.0101        ............................................................  420

Asn
Der p 2 variant T   CTGAAAATGTTGTCGTCACTGTTAAAGTTATGGGTGATAATGGTGTTTTGGCCTGTGCTA  480
Der p 2.0101        ..................................C.........................  480
                                                                       Asp Der p 2 variant T   TTGCTACTCATGCTAAAATCCGCGATTAAATTCAGCAAACAAACAAAATTTATTGATTTT  532
Der p 2.0101        ...........................---------........................  540

Der p 2 variant T   GTAATCA-AATCAATTGATTTTCTTTCCAAAAAAATAA-AAATAA------GGGAATTC  591
Der p 2.0101        .......C..ATG..................A..T......AATTTT........  591
```

VARIANT OF MITE ALLERGEN AND USES THEREOF

BACKGROUND OF THE INVENTION

The preset invention relates to a new variant of the Der p 2 allergen of house dust mites and uses thereof.

It has long been recognized that allergy to house dust mites is a cause of many diseases such as asthma, rhinitis, sinusitis, eczema, allergic dermatitis, anaphylaxis, conjunctivitis, and/or angioedema[1]. Specifically, *Dermatophagoides pteronyssinus* is one of the major species of house dust mites, and many studies have been performed to identify the allergens it produces. In this regard, Der p 2 has been recognized as a representative allergen produced by *D. pteronyssinus*. More than 80% of allergic patients react with Der p 2[3, 4].

Der p 2 exhibits long term stability in natural conditions[6] and is resistant to heat, pH, and various chemical denaturing treatments[7]. The three-dimensional structure of Der p 2 has been determined by NMR[8] and X-ray crystallography[9]. In particular, Der p 2 exhibits the immunoglobulin (Ig)-fold structure with two anti-parallel β-sheets. In addition, Der p 2 lacks the inter-sheet disulphide bond that links the strands B and F in the Ig-like domains; instead three disulphide linkages between residues 8 and 119, 21 and 27, and 73 and 78 are present. Moreover, the disulphide bond between residues 8 and 119 links the strands A' and G' together, and the other two disulphide bonds are located at the loop regions.

Der p 2 cDNA sequences have been identified, and the deduced amino acid sequences reveal that Der p 2 has 146 amino acid residues with a signal peptide of 17 residues. In addition, it is found that a significant degree of polymorphism exists in the DNA sequences of Der p 2[10, 11]. To date, there have been identified eight Der p 2 variants each of which has unique amino acid substitutions at the polymorphism residues[12]. They are useful in the study of immunopathogenesis of mite allergy and the development of reagents for diagnosis and treatment of mite allergy.

BRIEF SUMMARY OF THE INVENTION

We have isolated cDNA of a new allergen, named "Der p 2 variant T," by screening the *D. pteronyssinus* λgt11 cDNA library. The nucleotide sequence of the Der p 2 variant T cDNA has been identified and the recombinant Der p 2 variant T polypeptide has been produced in *E. coli* and *Pichia pastoris*. Der p 2 variant T is suitable for use in diagnosis and therapy of diseases.

As a first aspect according to the invention, there is provided a polynucleotide consisting of a nucleotide sequence encoding an amino acid sequence of SEQ ID NO: 1.

As a second aspect according to the invention, there is provided a recombinant nucleic acid comprising a nucleotide sequence encoding an amino acid sequence of SEQ ID NO: 1.

As a third aspect according to the invention, there is provided a transgenic organism comprising the polynucleotide or the recombinant nucleic acid as mentioned above.

As a forth aspect according to the invention, there is provided a polypeptide comprising an amino acid sequence of SEQ ID NO: 1.

As a fifth aspect according to the invention, there is provided a method for diagnosis of allergy to house dust mites in a subject comprising detecting if the subject reacts to the above mentioned polypeptide.

As a sixth aspect according to the invention, there is provided a composition for diagnosis of allergy to house dust mites in a subject comprising the above mentioned polypeptide and a diluent.

As a seventh aspect according to the invention, there is provided a method for treating or preventing an allergic disease in a subject comprising administrating the above mentioned polypeptide to the subject.

As an eighth aspect according to the invention, there is provided a pharmaceutical composition comprising the above mentioned polypeptide and a pharmaceutical acceptable excipient or carrier.

As a ninth aspect according to the invention, there is provided a DNA vaccine comprising the above mentioned polynucleotide or recombinant nucleic acid.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the preferred embodiments shown.

In the drawings.

DETAILED DESCRIPTION OF THE INVENTION

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant nucleic acid" refers to a polynucleotide or nucleic acid having sequences that are not naturally joined together. A recombinant nucleic acid may be present in the form of a vector. "Vectors" may contain a given nucleotide sequence of interest and a regulatory sequence. Vectors may be used for expressing the given nucleotide sequence or maintaining the given nucleotide sequence for replicating it, manipulating it or transferring it between different locations (e.g., between different organisms). Vectors can be introduced into a suitable host cell for the above mentioned purposes.

Examples of vectors include, but are not limited to, plasmids, cosmids, phages, YACs or PACs. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g., α-mating factor signal) and other control sequence (e.g., Shine-Dalgano sequences and termination sequences). Preferably, vectors may further contain a marker sequence (e.g., an antibiotic resistant marker sequence) for the subsequent screening procedure. More preferably, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes, but is not limited to, a His-tag fused polypeptide and a GST fused polypeptide.

The term "polypeptide" refers to a polymer composed of amino acid residues linked via peptide bonds. Polypeptides can be synthesized, for example, using an automated polypeptide synthesizer. The term "protein" typically refers to large polypeptides. The term "peptide" typically refers to short polypeptides.

Amino acids can be expressed by three letters or one letters. Table 1 lists standard amino acid abbreviations.

TABLE 1

Standard amino acid abbreviations

| Amino Acid | 3-Letter | 1-Letter |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "vaccine" refers to an agent or composition containing an active component effective to induce a therapeutic degree of immunity in a subject against a certain pathogen or disease. Traditionally, the active component of a vaccine is a polypeptide derived from a pathogen which is the target of the vaccine. The term "DNA vaccine" refers to a vaccine wherein the active component is DNAs.

The term "pharmaceutical composition" refers to a composition suitable for pharmaceutical use in a subject. A pharmaceutical composition comprises a pharmacologically effective amount of an active agent and a pharmaceutically acceptable carrier. "Pharmacologically effective amount"

refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "subject" in need of diagnosis or therapy is a human or non-human mammal. Non-human mammals include, but are not limited to, primates, ungulates, canines and felines.

We have isolated a cDNA molecule encoding a new variant of Der p 2, named "Der p 2 variant T," which is useful in diagnosis and therapy of allergic diseases, especially those in associated with Der p 2.

Figure 1:
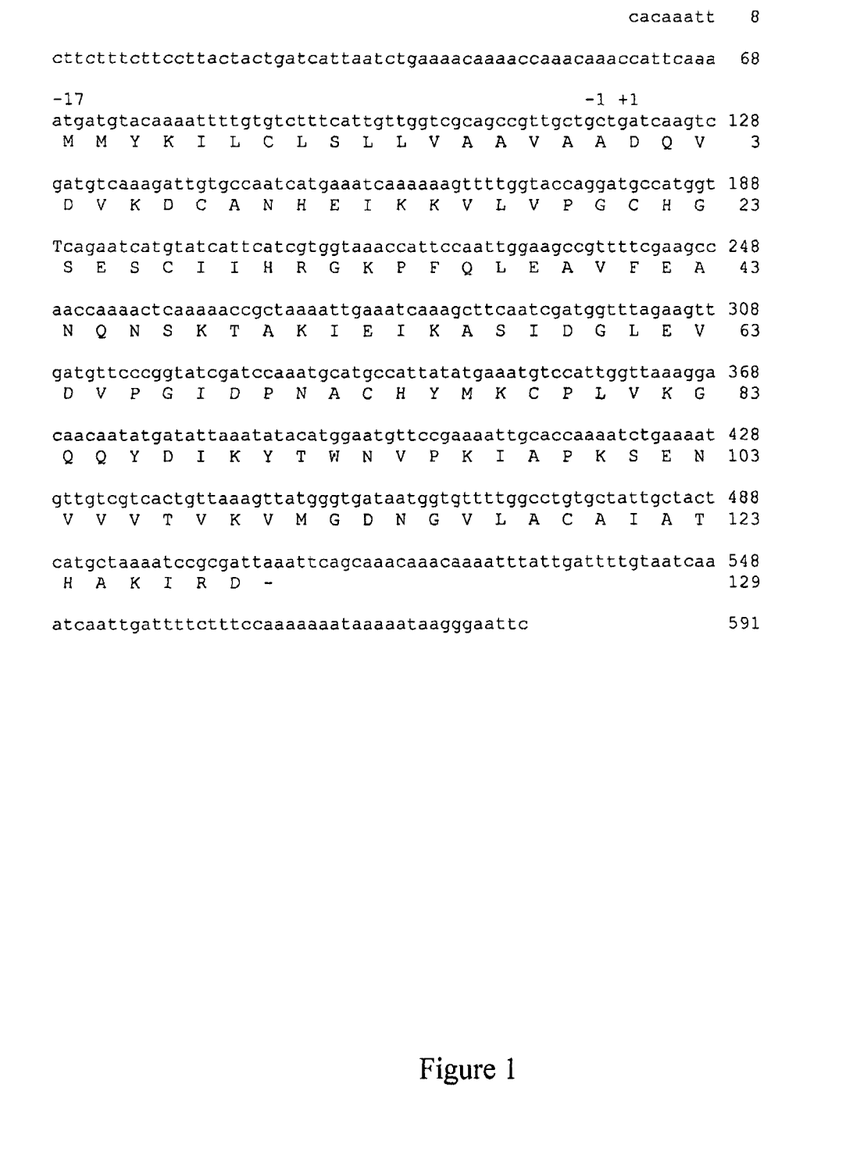
FIG. 1 represents the nucleotide sequence of the cDNA molecule of Der p 2 variant T (SEQ ID NO: 3, nucleotide positions 1 to 591) and the deduced amino acid sequence therefrom (SEQ ID NO: 1, amino acid positions −17 to 129) according to the invention.

FIG. 1 shows the cDNA nucleotide sequence and the deduced amino acid sequence (SEQ ID NO: 1) of Der p 2 variant T. Der p 2 variant T of the invention exhibits a significant diversity of nucleotide and amino acid sequences from other known Der p 2 variants. Table 2 shows a comparison between the amino acid substitutions at the polymorphic region of Der p 2 variant T and those of other known Der p 2 variants.

TABLE 2

List of polymorphic residues of Der p 2 variants*

|  | −1 | 26 | 40 | 47 | 98 | 111 | 114 | 116 | 127 |
|---|---|---|---|---|---|---|---|---|---|
| Der p 2.0101 | R | P | V | T | A | M | D | V | I |
| Der p 2.0102 | R | P | V | S | A | M | N | V | L |
| Der p 2.0103 | R | P | L | S | A | M | N | V | I |
| Der P 2.0104 | R | P | L | S | A | L | N | V | I |
| Der p 2.0105 | R | P | L | S | A | M | D | V | I |
| Der p 2.0106 | R | P | V | T | T | M | D | V | I |
| Der p 2.0107 | R | P | V | S | A | M | D | V | I |
| Der p 2.0108 | R | P | V | S | A | M | D | A | I |
| Der p 2 variant T | A | S | V | S | A | M | N | V | I |

*The amino acid numbering is based on the sequence Der p 2.0101 (accession number P49278).

Figure 2:
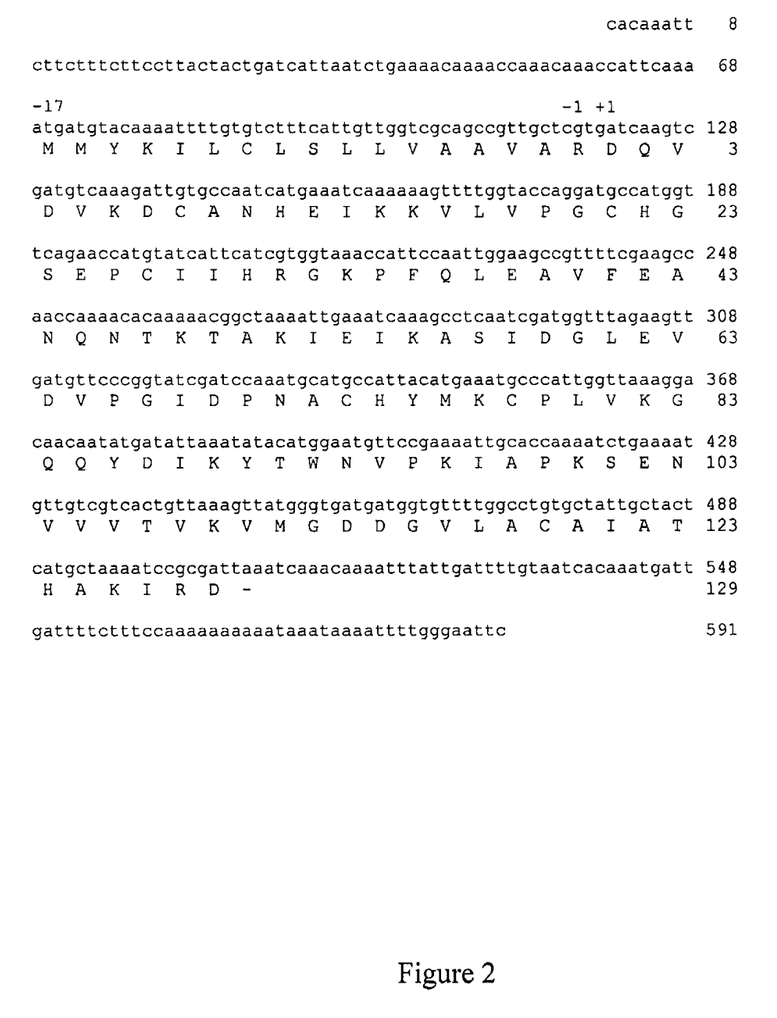
FIG. 2 represents the nucleotide sequence of the cDNA molecule of Der p 2.0101 (SEQ ID NO: 6, nucleotide positions 1-591; accession number: AF276239) and the deduced amino acid sequence therefrom (SEQ ID NO: 4, amino acid positions −17 to 129; accession number: P49278).

As shown in Table 2, Der p 2 variant T of the present invention reveals for the first time two new polymorphic amino acid residues at positions −1 and 26 which have not been identified in other known Der p 2 variant. At position −1, the amino acid residue of Der p variant T of the invention changes to Ala from Arg as in other known variant and at position 26, the amino acid residue of Der p variant T of the invention changes to Ser from Pro as in other known variant. More specifically, Der p 2 variant T of the invention comprises four amino acid changes i.e. Arg (−1) to Ala (−1), Pro 26 to Ser 26, Thr 47 to Ser 47, and Asp 114 to Asn 114 as compared with Der p 2.0101, the first Der p 2 isolated in 1989. FIG. 2 shows the nucleotide sequences (Accession Number: AF276239) and amino acid sequences (Accession Number: P49278) of Der p 2.0101. Such amino acid substitutions of Der p variant T of the invention makes its theoretical isoelectronic point higher (7.10) than that of Der p 2.0101 (6.56).

In one aspect, the present invention provides a polynucleotide consisting of a nucleotide sequence encoding an amino acid sequence of SEQ ID NO: 1. The polynucleotide of the invention can be used to produce Der p 2 T which is useful in diagnosis and therapy of allergic diseases as described above. In one embodiment, the polynucleotide consists of a nucleotide sequence of SEQ ID NO: 2.

The polynucleotide of the invention can be DNA or RNA, double stranded or single stranded. Where the polynucleotide is double stranded, both strands of the duplex (coding and complementary strands), either individually or in combination, are included in the invention. Where the polynucleotide is single stranded, it is to be understood that the complementary strand thereof is included as well. The invention also encompasses a degenerate version of the polynucleotide wherein at least one codon of the nucleotide sequence of the polynucleotide is substituted by a different codon, said at least one codon and said different codon encoding the same amino acid residue.

The polynucleotide of the invention may be produced using recombinant methods, synthetic methods or by any means available to those of skill in the art. It may also be cloned by standard techniques. Details for the isolation and preparation of the polynucleotide are described in the examples below.

In addition, the polynucleotide of the invention may be ligated to another polynucleotide to construct a recombinant nucleic acid which is used to, for example, amplify said polynucleotide.

Therefore, the present invention provides a recombinant nucleic acid which comprises a nucleotide sequence encoding an amino acid sequence of SEQ ID NO: 1 as described above. Specifically, the recombinant nucleic acid comprises a nucleotide sequence of SEQ ID NO: 2.

In one embodiment, the recombinant nucleic acid of the invention is a vector which is used for expressing or maintaining the nucleotide sequence as described above. The vector of the invention can be introduced into a suitable host cell to achieve the above mentioned purposes.

Preferably, the recombinant nucleic acid of the invention is an expression vector which can be used for producing Der p 2 variant T. Specifically, the expression vectors of the invention can be adapted for function in prokaryotes or eukaryotes by including appropriate promoters, replication sequences, markers, etc. for transcription and translation of mRNA.

In addition, the expression vectors of the invention can further contain an operator in the promoter region to control the initiation of the expression of the nucleotide sequence. Examples of the operator sequence are well known in the art. In one embodiment of the invention, the operator is an isopropyl-beta-D-thiogalactopyranoside (IPTG) or methanol inducible operator.

In addition, the expression vectors of the invention can further contain a tag sequence such that a fusion protein is produced to facilitate purification of the protein. For example, a polyhistidine tag sequence, e.g., six histidine residues, can be incorporated into the expression vector to produce a His-tag fused protein. The His-tag allows convenient isolation of the protein by nicle-chelate chromatography. For another example, a glutathione-S-transferase (GST) sequence is included in the expression vector so that a GST fused protein is produced and the subsequent purification of the protein can be conducted by using a glutathione (GSH) affinity column. Such tag sequence is well known in the art. Optionally, the tag fused to the polypeptide of interest can be removed by an enzymatic reaction, for example, to obtain said polypeptide itself.

The recombinant nucleic acid of the invention can be constructed by conventional genetic engineering techniques. Details regarding the construction of the recombinant nucleic acid of the invention are described in the examples below.

The polynucleotide of the invention or the recombinant nucleic acid of the invention can be introduced into an organism which is thus transformed to have a desired function of, for example, maintaining or expressing the nucleotide sequence as described above.

Accordingly, in yet another aspect, the present invention provides a transgenic organism which comprises the polynucleotide or the recombinant nucleic acid each of which comprising a nucleotide sequence encoding an amino acid sequence of SEQ ID NO: 1 as described above. Specifically, said nucleotide sequence is SEQ ID NO: 2. The organism can be used for, for example, maintaining said nucleotide sequence or producing a polypeptide comprising an amino acid sequence of SEQ ID NO: 1. Such organisms are also useful as a model for analyzing the effects of the allergen of the invention, for example.

As used herein, the term "transgenic organism" includes any suitable organism to which the above-mentioned polynucleotide or the recombinant nucleic acid is introduced. Examples of the organism range from lower order organism such as bacteria to higher order organisms such as plants and non-human mammals.

In one embodiment of the invention, the transgenic organism is a host cell which may be prokaryotic or eukaryotic. Examples of prokaryotic cells include, but are not limited to, bacteria such as *Escherichia coli*, lactobacilli and bifidobacteria. Eukaryotic cells can be, for example, insect, fungi, mammal or plant cells, preferably yeast cells, more preferably *Pichia pastoris*.

The host cells may be cultured under suitable conditions for expression of the polypeptide of interest. Expression of the polypeptides may be constitutive such that they are continually produced or inducible, requiring a stimulus to initiate expression. In the case of inducible expression, protein production can be initiated when desired by, for example, addition of an inducer substance to the culture medium, for example, IPTG or methanol. Polypeptide can be recovered and purified from host cells by a number of techniques known in the art, for example, chromatography e.g., HPLC or affinity columns.

In another embodiment of the invention, the transgenic organism is a plant, which includes, but is not limited to, crop plants such as rice, wheat, barley, sorghum, maize and oats, and economic plants such as tomatoes and bananas.

In yet another embodiment of the invention, the transgenic organism is a multicellular fungus, which includes, but is not limited to, mushrooms, preferably edible mushrooms such as gold needle mushrooms.

In yet another embodiment of the invention, the transgenic organism is a non-human transgenic animal, in particular, a mammal, whose germ cells (i.e. oocytes or sperm) comprises the above-mentioned polynucleotide or the recombinant nucleic acid according to the invention. Examples of transgenic animals include, but are not limited to, mice, guinea pigs, rabbits, pigs, sheep and cattle.

The introduction, into the organism (transformation), of the nucleic acid according to the invention, can be effected in principle by all methods with which the skilled persons is familiar.

Methods for introducing nucleic acids into host cells such as calcium chloride treatment, electroporation, DEAE-dextrin-mediated transfection, lipofection and microinjection are well known in the art, and described in, for example, Int Arch Allergy Appl Immunol 1990; 91(2):118-23[5].

In the case of plants, the method which have described for the transformation and regeneration of plants from plant tissues or plant cells can be exploited for transient or stable transformation. Suitable methods are the biolistic method or by protoplast transformation, electroporation, microinjection and the *agrobacterium*-mediated gene transfer. The above methods may be applied to fungi transformation as well. Such methods are described, for example, in Methods Mol Biol. 2004; 267:329-50.[25]

In the case of transgenic animals of the invention, they may be produced, for example, by introducing the recombinant nucleic acid molecule into a fertilized egg or embryonic stem (ES) cell, typically by microinjection, electroporation, lipofection, particle-mediated gene transfer. The transgenic organisms express the heterologous nucleotide sequence in tissues depending upon whether the promoter is inducible by a signal to the cell, or is constitutive. The above methods are described, for example, in Curr Drug Deliv. 2004; 1(2): 165-93.[26]

In yet another aspect, the present invention provides a purified polypeptide comprising an amino acid sequence of SEQ ID NO: 1 (i.e. Der p 2 variant T). As mentioned above, a tag sequence (e.g. a GST sequence) can be included in the expression vector of the invention so as to produce a fusion protein.

The polypeptide of the invention may be produced by a recombinant method e.g., culturing the host cells which comprise the expression vector of the invention under suitable conditions and recovering and purifying the polypeptide as mentioned above. The polypeptide of the invention may also be produced by a chemical synthesis method which is conducted by coupling the carboxyl group (C-terminus) of one amino acid to the amino group (N-terminus) of another. Examples of the chemical synthesis method include, but are not limited to, a solid-phase synthesis such as t-Boc solid-phase peptide synthesis and Fmoc solid-phase peptide synthesis.

The polypeptide of the invention contains 129 amino acid residues (positions 1 to 129) with a signal peptide of 17 residues at the amino terminal (positions −17 to −1). Particularly, the amino acid residue at position −1 of the polypeptide of the invention is Ala which is different from Arg as shown in other known Der p 2 variants, and the amino acid residue at position 26 of the polypeptide of the invention is Ser which is different from Pro as shown in other known variants. More particularly, the polypeptide of the invention comprises four amino acid changes i.e. Arg (−1) to Ala (−1), Pro 26 to Ser 26, Thr 47 to Ser 47, and Asp 114 to Asn 114 when compared with the specific known variant, Der p 2.0101.

The genetic engineering relevant techniques used herein such as polynucleotide synthesis, polymerase chain reaction (PCR), cloning, vector construction, cell transformation, protein expression, peptide synthesis and purification, are well known in the art and described in, for example, Int Arch Allergy Appl Immunol 1990; 91(2):118-23[5].

We have shown in the following examples that the allergic patients have higher reactivity to the polypeptide of the invention than that of the conventional Der p 2 variant. The polypeptide of the invention is thus useful in diagnosis and treatment of allergy to house dust mites.

Accordingly, in another aspect, the invention provides a method for diagnosis of allergy to house dust mites in a subject which comprises detecting if the subject reacts to the polypeptide of the invention. Specifically, the subject is suffered from asthma, rhinitis, sinusitis, eczema, allergic dermatitis, anaphylaxis, conjunctivitis, and/or angioedema.

In one embodiment, said detecting is performed using an in vitro immunoassay. The term "immunoassay" refers to a biochemical test that determine the concentration or presence of a substance in a biological sample based on the reaction of specific interaction of an antibody to its antigen. The methodology for the assays is conventional in the art. Typical examples of the immunoassay include, but are not limited to, a dot-blot immunoassay, a radioimmunoassay (RIA), an enzyme immunoassay (EIA), and a particle agglutination immunoassay.

Specifically, according to the invention, the immunoassay is carried out on a sample obtained from the subject, determining if the sample carries antibodies reactive with the polypeptide of the invention. More specifically, the sample is sera from the subject. Even more specifically, the antibodies to be determined are IgE.

In one specific example, the method of the invention comprises applying the polypeptide of the invention onto a nitrocellulose membrane, adding sera obtained from the human to the membrane and incubating it for a period of time, washing the membrane, adding radiolabeled anti-human IgE to the membrane and incubating it for another period of time, washing the membrane, developing a signal from the membrane and measuring it with a proper device, and determining if the subject reacts to the polypeptide based on the measured signal. It is then confirmed that the subject is allergic to house dust mites in case he/she reacts with the polypeptide.

In another embodiment, said detecting according to the invention is performed using a skin prick test. A skin prick test is commonly used to determine allergy which usually involves placing a small amount of a suspected allergen on the skin of a subject in need thereof and then pricking the skin such that the allergen is introduced under the skin surface. The skin is then observed for signs of an inflammatory reaction, such as swelling and redness of the site. The methodology for the skin prick test is conventional in the art.

In one specific example, the method of the invention comprises applying the polypeptide of SEQ ID NO: 1 onto the subject's skin, pricking the subject's skin, observing if an inflammation reaction (e.g., itching, erythema, weal and flare response) develops on the skin, measuring the area of the inflammation reaction, determining if the subject reacts to the polypeptide based on the measured size of the area. It is then confirmed that the subject is allergic to house dust mites in case he/she reacts to the polypeptide. Particularly, the polypeptide of the invention is dissolved in normal saline, a drop of the polypeptide solution is applied on the volar of the forearm of the subject, and the skin is pricked with a disposable lancet. More particularly, a wheal reaction of greater than 3 mm×3 mm in size is regarded as a positive reaction of the skin prick test.

In yet another aspect, the present invention provides a composition or reagent comprising a polypeptide of SEQ ID NO: 1 for use in the above-mentioned methods. The composition or reagent of the invention can be easily prepared, for example, by mixing the polypeptide with a suitable diluent such as saline.

It is known that allergic diseases can be treated by specific hyposensitizing immunotherapy (SIT) which includes administrating increasing doses of the allergens that trigger the allergic reactions, thus inducing gradual desensitization to said substance in the patient.

Accordingly, the present invention further provides a method for treating or preventing an allergic disease in a subject comprising administrating the polypeptide of SEQ ID NO: 1 to the subject. Preferably, the allergic disease is in associated with house dust mites, which includes, but are not limited to, asthma, rhinitis, sinusitis, eczema, allergic dermatitis, conjunctivitis, anaphylaxis, and/or angioedema.

A further aspect of the invention relates therefore to a pharmaceutical composition comprising an effective amount of the polypeptide of the invention, together with a pharmaceutically acceptable excipient. The pharmaceutical composition of the invention can be used in the above mentioned treatments.

In making the pharmaceutical composition of the invention, the polypeptide of the invention as the active ingredient is usually diluted with an excipient and/or enclosed within a carrier which can be in the form of a capsule, sachet, paper or other container. The excipient employed is typically an excipient suitable for administration to human subjects or other mammals. Some examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. In addition, the pharmaceutical composition of the invention can be in the form of tablets, pills, powders, suspensions, emulsions, solutions, syrups, aerosols (as a solid or in a liquid medium), ointments, capsules, or sterile packaged powders. Furthermore, the pharmaceutical composition of the invention can be administered to a subject by a proper route such as an oral route or a parenteral route.

In a specific embodiment, said pharmaceutical composition is a vaccine for use in the prophylactic treatment of the allergic diseases. Vaccination principles and practice are well known to those skilled in the art and described in, for example, Int Arch Allergy Immunol 2006; 139:332-345[21].

In addition, the polynucleotide or recombinant nucleic acid of the invention as mentioned above may be administrated to a subject in the form of a DNA vaccine. Therefore, the present invention further relates to a DNA vaccine which comprises a polypeptide consisting of a nucleotide sequence encoding an amino acid sequence of SEQ ID NO: 1 or a recombinant nucleic acid comprising a nucleotide sequence encoding an amino acid sequence of SEQ ID NO: 1 as previously described. Preferably, the nucleotide sequence is SEQ ID NO: 2. Preparation of a DNA vaccine and vaccination thereof are well known in the art and are described in, for example, Nat Med. 1996 May; 2(5):540-4[22].

The present invention will now be described more specifically with reference to the following embodiments, which are provided for the purpose of demonstration rather than limitation.

Example 1

Isolation of cDNA of Der p 2 Variant T

The cDNA of the new Der p 2 variant T protein was isolated by screening the *D. pteronyssinus* λgt11 cDNA library with Taiwanese asthmatic children's sera by IgE plaque radioimmunoassay. The host *E. coli* strain Y1090 was grown in Luria-Bertani (LB) broth supplemented with 0.2% maltose and 10 mM MgSO4 with vigorous shaking at 37° C. The overnight-saturated culture was spun down and then gently resuspended in 0.5 volumes of 10 mM $MgSO_4$. For each 150 mm Petri dish with solidified LB agar, 300 μl of the Y1090 overnight-saturated culture were incubated with 10,000 pfus of lambda-gt11 phage at room temperature for 30 minutes without shaking and then plated on LB agar in 7-7.5 ml 0.7% top agar. After the top agar solidified, the Petri dishes were incubated at 42° C. for 3 hours. When plaques became visible, an isopropyl 1-thio-β-D-galactopyranosid (IPTG) soaked nitrocellulose membrane was placed on each Petri dish and continued the incubation at 37° C. for overnight. The membranes were removed from plates and washed three times in 10 mM Tris-HCl, 0.15 M NaCl, 0.05% Tween-20, pH 7.5 (TBST) for 5 minutes each at room temperature. The membranes were blocked with 5% non-fat milk in TBST for 1 hour and washed three times in TBST. The sera were adsorbed in 1:1 ratio with an *E. coli* extract at 4° C. for overnight and clarified by centrifugation to reduce anti-*E. coli* antibody background. The sera were incubated with the milk blocked membranes at 4° C. for overnight. The membranes were developed with $^{125}$I-labeled mouse monoclonal anti-human IgE (Silenus Laboratories, Hawthorn, Victoria, Australia) for 2 hours at room temperature followed by four washes with TBST. The membranes were autoradiographed with intensifying screens at −80° C. for two days. Positive plaques were excised from the 150 mm agar plates, re-plated in 90 mm Petri dishes and repeated the screening procedure to confirm the positive IgE reactive clones.

As a result, a new Der p 2 cDNA clone was isolated. The cDNA molecule encodes a new Der p 2 variant protein designated as "Der p 2 variant T" (FIG. 1). It contains four polymorphic amino acids as compared to the reference Der p 2 protein sequence of Der p 2.0101, the first Der p 2 isolated in 1989 (FIG. 2, Accession Number: P49278). These polymorphic residues include changes at Arg(−1) to Ala(−1), Pro26 to Ser26, Thr47 to Ser 47, and Asp114 to Asn 114 and make the theoretical isoelectronic point raised from 6.56 (Der p 2.0101) to 7.10 (Der p 2 variant T). The comparison of all the polymorphism of Der p 2 variant T with eight known variants is shown in Table 1 (see above).

Related nucleotide and amino acid sequences of the Der p 2 variants and positions thereof are described in Table 3.

TABLE 3

Descriptions for the nucleotide and amino acid sequences of Der p 2 variants

| SEQ ID No | Description | Positions* |
|---|---|---|
| 1 | Der p 2 variant T protein | amino acid positions −17 to 129 |
| 2 | Der p 2 variant T cDNA | nucleotide positions 69 to 566 |
| 3 | Der p 2 variant T cDNA | nucleotide positions 1 to 591 |
| 4 | Der p 2.0101 protein | amino acid positions −17 to 129 |
| 5 | Der p 2 2.0101 cDNA | nucleotide positions 69 to 566 |
| 6 | Der p 2 2.0101 cDNA | nucleotide positions 1 to 591 |

*The positions of the nucleotides and amino acids refer to FIGS. 1 and 2.

Figure 3:
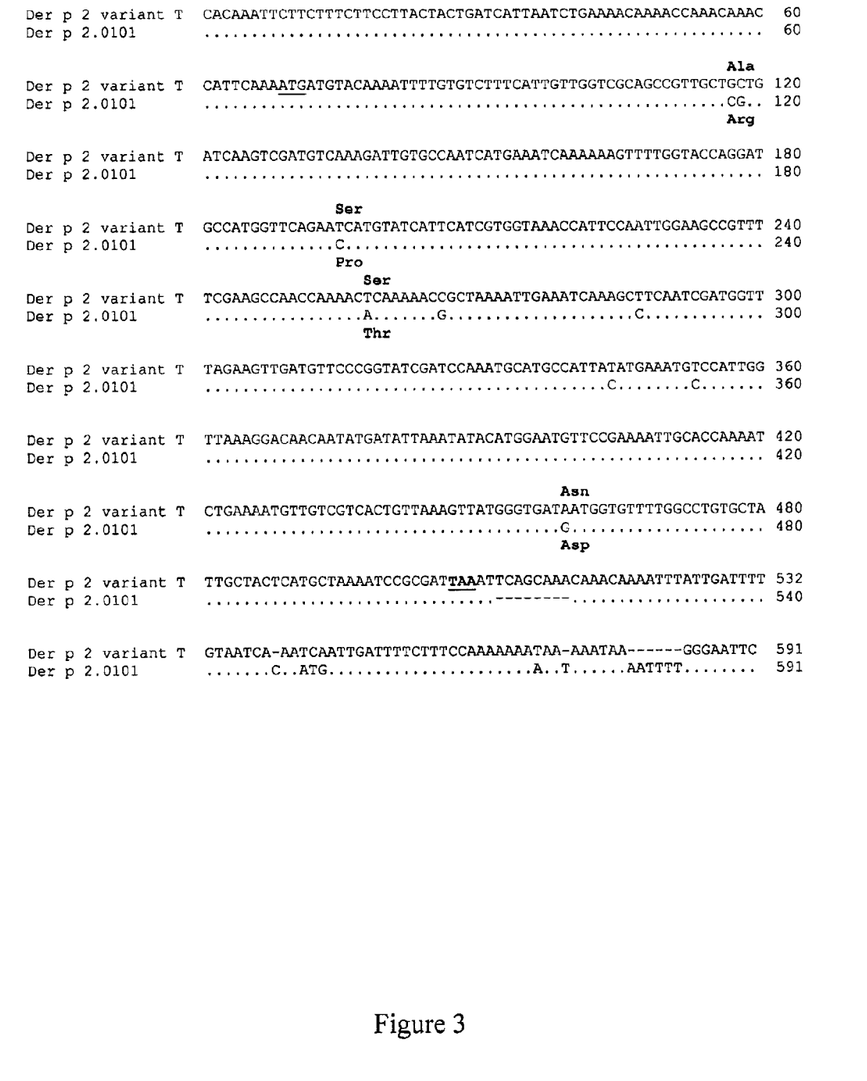
FIG. 3 shows the alignment between the nucleotide sequence of Der p 2 variant T (SEQ ID NO: 3) and that of Der p 2.0101 (SEQ ID NO: 6), wherein the amino acid residues indicated on the top and bottom of the nucleotide sequence are unique amino acid substitutes for Der p 2 variant T and that of Der p 2.0101, respectively; the start and stop codons are underlined; the symbol "•" indicates the same nucleotide; the symbol "−" means a space; and the shadowed part refers to the 3' untranslated nucleotide sequence.

All the residue changes except Ser26 have been found in other known Der p 2 variants with different combination. The Pro26Ser change is at a new polymorphic residue in Der p 2 and has not been identified to date. The 5' untranslated nucleotide sequence of Der p 2 variant T is identical to that of Der p 2.0101. The coding region (open reading frame) contains several polymorphic nucleotide changes and the 3' untranslated nucleotide sequence shows high degree of variation (FIG. 3).

Example 2

Plasmid Construction and Expression of Der p 2 Variants in *E. coli*

The cDNAs coding for both the mature Der p 2 variants were amplified with the forward primer pDp2-5'BamHI and reverse primer pDp2-3'EcoRI by polymerase chain reaction (PCR). The PCR product was ligated into the BamHI and EcoRI sites of pGEX-2T vector (Pharmacia, Uppsala, Sweden) and the expression construct was transformed into *E. coli* strain TG1. Fusion protein production was induced with 0.1 mM IPTG at 30° C. for 1 hour and purified by glutathione agarose (Sigma, St. Louis, Mo., USA) affinity chromatography as described previously for the Der p 2.0101[5]. The recombinant protein was produced as a fusion protein with glutathione-S-transferase (GST). All the primer sequences are listed in Table 3.

TABLE 3

Primers used for construction of expression plasmids

| SEQ ID No | Primer | Sequence |
|---|---|---|
| 7 | pDp2-5'BamHI | 5'-GC<u>GGATCC</u>GATCAAGTCGATGT CAAA-3' |
| 8 | pDp2-5'KEX2 | 5'-GC<u>CTCGAG</u>AAAAGAGATCAAGT CGATGTCAAA-3' |
| 9 | pDp2-3'EcoRI | 5'-GC<u>GAATTC</u>TTAATCGCGGATTT TAGC-3' |

*Restriction enzyme sites are underlined.

Figure 4:
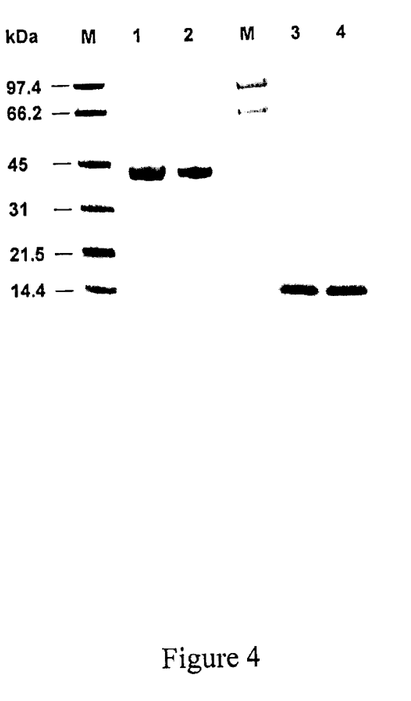
FIG. 4 shows the results of the SDS-PAGE analysis, wherein Lane 1 represents the GST-Der p 2.0101 fusion protein from the *E. coli* expression system; Lane 2 represents the GST-Der p 2 variant T fusion protein from the *E. coli* expression system; Lane 3 represents the Der p 2.0101 protein from *P. pastoris* expression; Lane 4 represents the Der p 2 variant T protein from *P. pastoris* expression system; and M represents the molecular weight markers.

The cDNA encoding the mature Der p2.0101 and Der p2 variant T were subcloned in BamHI and EcoRI sites of pGEX-2T and expressed as fusion proteins with GST in *E. coli* strain TG1. The GST fusion proteins were affinity purified using glutathione agarose beads from the soluble fraction as described, and examined by SDS-PAGE following by silver staining (FIG. 4).

Example 3

Plasmid construction and Expression of Der p 2 Variant T in *Pichia pastoris*

The cDNAs of the mature Der p2 variants were amplified by polymerase chain reaction (PCR) from the plasmid pGEX-2T-Der p 2[19] using the forward primer pDp2-5'KEX2 and reverse primer pDp2-3'EcoRI (Table 3). The 5' XhoI and 3' EcoRI sites were used for directional in-frame cloning with the α-factor signal sequence driven by the alcohol oxidase gene (AOX1) promoter in pPIC9 vector. The PCR reaction was carried out with pfu DNA polymerase and the insert in pPIC9 was completely sequenced. The pPIC9 vector provided the α-mating factor signal for secretion and the HIS4 gene for selection of recombinant clones. Both the pPIC9-Der p 2.0101 and pPIC9-Der p 2 variant T were linearized with BglII and transformed into *P. pastoris* strain GS115 by lithium chloride method as described in the *Pichia expression manual* (version E) (Invitrogen, Carlsbad, Calif., USA). The His$^+$ colonies were further selected on two different media: one with methanol (MM) and the other with glucose (MD) as the sole carbon source. Clones with homologous recombination at the AOX1 gene exhibit slow growing in MM medium and are phenotypically Mut$^s$ (methanol utilization slow). Those Mut$^s$ clones were selected for screening of protein expression.

Typically the soluble secretory recombinant Der p 2 proteins were detectable 4 hours after methanol induction as detected by Coomassie blue stained SDS-PAGE. The protein production continued to increase up to 96 hours and optimum yield was obtained at 48 hours post-induction. The recombinant Der p 2 proteins were then purified to homogeneous with cation-exchange chromatography.

Example 4

Purification of Der p 2 Variants from *Pichia pastoris* Expression System

The yeast media containing the recombinant Der p 2.0101 or Der p 2 variant T were applied to a Sephadex G25 molecular sieving column (5×20 cm) equilibrated with 20 mM sodium acetate, pH 5.5. Recombinant Der p 2-containing fractions were pooled and applied to a SP-Sepharose column (2.6×15 cm) equilibrated with the previous buffer. Bound proteins were eluted with 600 ml of a linear sodium chloride gradient from 0 to 500 mM. The culture media of the three disulphide bond disrupted Der p 2 mutants were equilibrated to 20 mM sodium acetate, pH 5.5 buffer by dialysis. Precipitates were removed by centrifugation at 12,000 g for 10 minutes. The Hi-Trap SP-Sepharose columns (5 ml, Pharmacia) were used for purification of the mutants. The bound proteins were eluted by a sodium chloride gradient from 0 to 1 M in 50 ml. The purity of recombinant Der p 2 was examined by SDS-PAGE followed by silver staining as shown in FIG. 4. The final yields of the recombinant Der p 2.0101 and Der p 2 variant T were above 500 mg/L by shaking flask culture method.

In addition, both of the recombinant Der p 2 proteins started at +1 position as determined by N-terminal peptide sequencing. That indicated the correct recognition and processing of the designed junction between the yeast signal peptide and the first residue of Der p 2.

In this invention, large quantities of good quality recombinant Der p 2 variants were produced successfully in methylotrophic yeast *Pichia pastoris*. There are several advantages of using *P. pastoris* in comparison to *S. cerevisiae*. Firstly, the protein produced in *P. pastoris* is less hyperglycosylated. Secondly, the length of the oligosaccharide chain added to the protein in *P. pastoris* is much shorter than that in *S. cerevisae*. Thirdly, the *S. cerevisae* core oligosaccharides have terminal alpha 1,3 mannose linkages whereas *P. pastoris* does not. The lack of the antigenic alpha 1,3 mannose linkages in *P. pastoris*-produced protein makes it more suitable for diagnostic and therapeutic application as well as for in vivo animal studies. To date this expression has been used successfully by many researchers to produce heterologous proteins in extremely high yield[18]. The *P. pastoris* yeast expression system was exploited to produce soluble recombinant Der p 2 with high yield and to avoid the endotoxin contamination of the recombinant proteins. The large quantity of recombinant Der p 2 proteins greatly facilitated the in vivo and in vitro immunological studies.

Example 5

Human IgE Dot Immunoblot

The 50 sera samples from doctor diagnosed asthmatic children (aged between 7 to 15 years), who did not receive immunotherapy, were provided by late Professor Kue-Hsiung Hsieh from the Allergy Clinic of Department of Pediatrics, National Taiwan University Hospital, Taipei, Taiwan.

Figure 5:
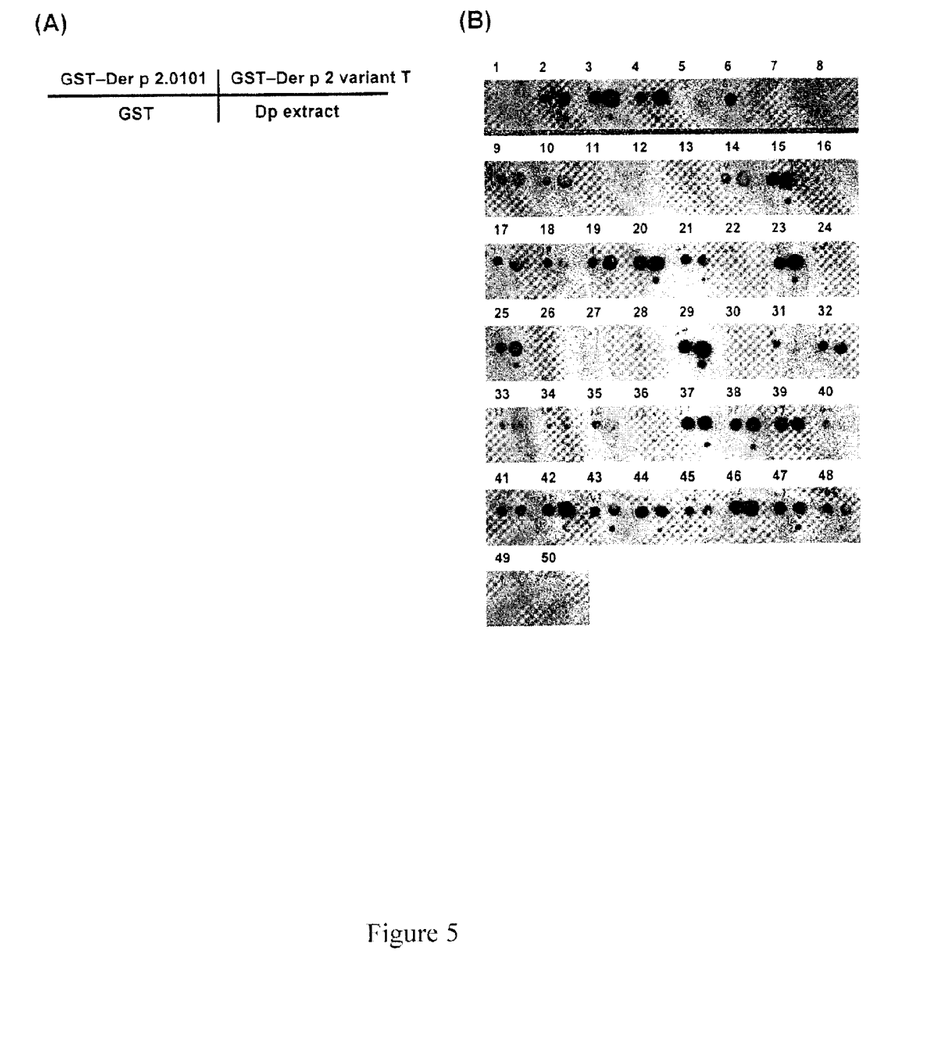
FIG. 5 relates to the IgE dot-blot immunoassay, wherein (A) shows the positions of the protein samples, the GST-Der p 2.0101 fusion protein, the GST-Der p 2 variant T fusion protein, the GST peptide, and the *D. pteronyssinus* extract, loaded on the nitrocellulose membrane; (B) shows the results of the immunoassay, numbers 1 to 50 independently representing sera samples from the 50 patients; and (C) shows the level of IgE reactivity of the protein samples quantified by densitometry.

A dot-blot immunoassay for IgE was performed by a protocol previously described[23]. Two micrograms of purified GST-Der p 2.0101, GST-Der p 2 variant T and GST proteins (a negative control) were applied onto nitrocellulose membrane in duplicate. The *D. pteronyssinus* mite extract was included as a positive control using 5 μg/dot. FIG. 5(A) shows the positions of the protein samples loaded onto the membrane. The membranes were then washes three times with TBST and blocked with 5% skim milk in TBST at room temperature at 1 hour. After three washes with TBST, allergic asthma children' sera (panel 1) were diluted 1:5 in TBS and incubated with the dot-blots at 4° C. for 12-16 hours. The secondary antibody, $^{125}$I-labeled mouse monoclonal anti-human IgE (Silenus Laboratories), was incubated at room temperature at 1 hour. The signal of the reaction was developed after four washes with TBST by autoradiography. The film was scanned with a GS-700 densitometer and analyzed with the Molecular Analysis software (Bio-Rad, Hercules, Calif., USA). Statistical differences were determined using SPSS, Version 11.0.1 (SPSS Inc., Chicago, Ill.). Correlations were analyzed using the Spearman's rank method. A P-value of less than 0.05 was considered statistically significant.

As shown in FIG. 5B, the sera of the patients 34, 31, and 31 reacted positively with GST-Der p 2.0101, GST-Der p 2 variant T, and *D. pteronyssinus* extract, respectively. There was no reactivity registered to GST protein alone. Some sera (e.g. sera of patients 3 and 4) showed higher reactivity to GST-Der p 2 variant T; while others (e.g. sera of patients 6 and 31) showed exclusive reactivity to GST-Der p 2.0101. Densitometry analysis revealed significantly higher IgE reactivity of GST-Der p 2 variant T than that of GST-Der p 2.0101 in this panel of sera (P=0.037) (FIG. 5C). In other words, Der p 2 variant T showed higher IgE reactivity with a significant number of sera tested as compared with that of Der p 2.0101 variant. Such observation was also demonstrated by skin prick tests performed on asthmatic children (see below).

Example 6

Skin Prick Tests

Skin prick tests were performed on nine asthmatic children according to the procedures described previously[24]. Purified GST-Der p 2.0101 and GST-Der p 2 variant T proteins were dissolved in normal saline and used for skin prick test at the concentration of 25 μg/ml. A drop of 10 μl of protein solution was applied on the volar of the forearm and the skin was pricked with a disposable lancet. Histamine (1 mg/ml) and normal saline were included as positive and negative controls. The lengths and widths of wheal and erythema were measured after 30 minutes. A wheal reaction of greater than 3 mm×3 mm in size after subtracting the negative control was regarded as a positive skin reaction. The results are shown in Table 4.

TABLE 4

Skin prick tests of nine asthmatic children with Der p 2 variants

| | | Wheal/Erythema (mm × mm) | | |
|---|---|---|---|---|
| Subject | GST | D. pteronyssinus extract | GST-Der p 2.0101 | GST-Der p 2 variant T |
| 1 | −/− | 11 × 12/25 × 25 | 10 × 8/25 × 22 | 15 × 15/30 × 25 |
| 2 | −/− | 9 × 8/33 × 30 | 11 × 10/23 × 22 | 13 × 10/30 × 25 |
| 3 | −/− | 11 × 11/35 × 27 | 7 × 7/23 × 22 | 12 × 12/36 × 37 |
| 4 | −/− | −/− | 7 × 6/13 × 12 | 11 × 9/28 × 18 |
| 5* | −/− | 10 × 11/20 × 18 | −/− | 11 × 10/25 × 18 |
| 6* | −/− | 7 × 7/34 × 30 | −/− | 11 × 8/29 × 30 |
| 7* | −/− | 7 × 7/9 × 11 | −/− | 9 × 9/12 × 12 |
| 8* | −/− | −/− | −/− | 9 × 8/12 × 12 |
| 9 | −/− | −/− | −/− | −/− |

−: negative skin prick test response.
*subjects showed positive reactivity to Der p 2 variant T only.

As shown in Table 4, the skin reactivity of GST-Der p 2 variant T is higher than that of GST-Der p 2.0101 in the subjects tested, and four of the asthmatic children (Subjects 5 to 8) reacted with Der p 2 variant T only.

All publications and patent documents cited in this application are incorporated by reference in their entirety for all purposes to the same extent as if each individual publication or patent document were so individually denoted.

REFERENCES

[1] Sporik R, Chapman M D, Platts-Mills T A. House dust mite exposure as a cause of asthma. Clin Exp Allergy 1992; 22(10):897-906.

[2] Platts-Mills T A, Vervloet D, Thomas W R, Aalberse R C, Chapman M D. Indoor allergens and asthma: report of the Third International Workshop. J Allergy Clin Immunol 1997; 100(6 Pt 1):52-24.

[3] Lind P, Lowenstein H. Identification of allergens in *Dermatophagoides pteronyssinus* mite body extract by crossed radioimmunoelectrophoresis with two different rabbit antibody pools. Scand J Immunol 1983; 17(3):263-73.

[4] Heymann P W, Chapman M D, Aalberse R C, Fox J W, Platts-Mills T A. Antigenic and structural analysis of group II allergens (Der f II and Der p II) from house dust mites (*Dermatophagoides* spp). J Allergy Clin Immunol 1989; 83(6):1055-67.

[5] Chua K Y, Doyle C R, Simpson R J, Turner K J, Stewart G A, Thomas W R. Isolation of cDNA coding for the major mite allergen Der p II by IgE plaque immunoassay. Int Arch Allergy Appl Immunol 1990; 91(2):118-23.

[6] de Boer R, van der Hoeven W A, Stapel S O. The decay of house dust mite allergens, Der p I and Der p II, under natural conditions. Clin Exp Allergy 1995; 25(8):765-70.

[7] Lombardero M, Heymann P W, Platts-Mills T A, Fox J W, Chapman M D. Conformational stability of B cell epitopes on group I and group II *Dermatophagoides* spp. allergens. Effect of thermal and chemical denaturation on the binding of murine IgG and human IgE antibodies. J Immunol 1990; 144(4):1353-60.

[8] Mueller G A, Benjamin D C, Rule G S. Tertiary structure of the major house dust mite allergen Der p 2: sequential and structural homologies. Biochemistry 1998; 37(37):12707-14.

[9] Derewenda U, Li J, Derewenda Z, Dauter Z, Mueller G A, Rule G S et al. The crystal structure of a major dust mite allergen Der p 2, and its biological implications. J Mol Biol 2002; 318(1):189-97.

[10] Chua K Y, Huang C H, Shen H D, Thomas W R. Analysis of sequence polymorphism of a major mite allergen, Der p 2. Clin Exp Allergy 1996; 26(7):829-37.

[11] Smith W A, Hales B J, Jarnicki A G, Thomas W R. Allergens of wild house dust mites: environmental Der p 1 and Der p 2 sequence polymorphisms. J Allergy Clin Immunol 2001; 107(6):985-92.

[12] Hales B J, Hazell L A, Smith W, Thomas W R. Genetic variation of Der p 2 allergens: effects on T cell responses and immunoglobulin E binding. Clin Exp Allergy 2002; 32(10):1461-7.

[13] Chua K Y, Dilworth R J, Thomas W R. Expression of *Dermatophagoides pteronyssinus* allergen, Der p II, in *Escherichia coli* and the binding studies with human IgE. Int Arch Allergy Appl Immunol 1990; 91(2):124-9.

[14] Smith A M, Chapman M D. Reduction in IgE binding to allergen variants generated by site-directed mutagenesis: contribution of disulfide bonds to the antigenic structure of the major house dust mite allergen Der p 2. Mol Immunol 1996; 33(4-5):399-405.

[15] Mueller G A, Smith A M, Williams D C, Jr., Hakkaart G A, Aalberse R C, Chapman M D et al. Expression and secondary structure determination by NMR methods of the major house dust mite allergen Der p 2. J Biol Chem 1997; 272(43):26893-8.

[16] Hakkaart G A, Aalberse R C, Van Ree R. Expression of the house dust mite allergen Der p2 and mutants in the baker's yeast *Saccharomyces cerevisiae*. Adv Exp Med Biol 1996; 409:395-8.

[17] Hakkaart G A, Harmsen M M, Chua K Y, Thomas W R, Aalberse R C, Van Ree R. Expression of the house dust mite allergen Der p 2 in the baker's yeast *Saccharomyces cerevisiae*. Clin Exp Allergy 1998; 28(1):45-52.

[18] Schmidt M, Hoffman D R. Expression systems for production of recombinant allergens. Int Arch Allergy Immunol 2002; 128(4):264-70.

[19] Ball T, Sperr W R, Valent P, Lidholm J, Spitzauer S, Ebner C et al. Induction of antibody responses to new B cell epitopes indicates vaccination character of allergen immunotherapy. Eur J Immunol 1999; 29(6):2026-36.

[20] Moverare R, Elfman L, Vesterinen E, Metso T, Haahtela T. Development of new IgE specificities to allergenic components in birch pollen extract during specific immunotherapy studied with immunoblotting and Pharmacia CAP System. Allergy 2002; 57(5):423-30.

[21] Weiss R, Scheiblhofer S, Gabler M, et al. Is genetic vaccination against allergy possible? Int Arch Allergy Immunol 2006; 139:332-345.

[22] Hsu C H, Chua K Y, Tao M H, Lai Y L, Wu H D, Huang S K, and Hsieh K H. Immunoprophylaxis of allergen-induced immunoglobulin E synthesis and airway hyperresponsiveness in vivo by genetic immunization. Nat Med. 1996 May; 2(5):540-4.

[23] Greene W K, Chua K Y, Stewart G A, and Thomas W R. Antigenic analysis of group I house dust mite allergens using random fragments of Der p I expressed by recombinant DNA libraries. Int Arch Allergy Appl Immunol. 1990; 92(1):30-8.

[24] Kuo I C, Cheong N, Trakultivakorn M, Lee B W, and Chua K Y. An extensive study of human IgE cross-reactivity of Blo t 5 and Der p 5. J Allergy Clin Immunol. 2003 March; 111(3):603-9.

[25] Lorence A, Verpoorte R. Gene transfer and expression in plants. Methods Mol Biol. 2004; 267:329-50.

[26] Azzam T, Domb A J. Current developments in gene transfection agents. Curr Drug Deliv. 2004 April; 1(2):165-93.

We claim:
1. An isolated polypeptide comprising SEQ ID NO: 1.
2. A composition comprising the polypeptide of claim 1.

\* \* \* \* \*

SEQUENCE LISTING

<160> NUMBER OF SEQ ID NOS: 9

<210> SEQ ID NO 1
<211> LENGTH: 146
<212> TYPE: PRT
<213> ORGANISM: Dermatophagoides pteronyssinus

<400> SEQUENCE: 1

Met Met Tyr Lys Ile Leu Cys Leu Ser Leu Leu Val Ala Ala Val Ala
1               5                   10                  15

Ala Asp Gln Val Asp Val Lys Asp Cys Ala Asn His Glu Ile Lys Lys
            20                  25                  30

```
Val Leu Val Pro Gly Cys His Gly Ser Glu Ser Cys Ile Ile His Arg
            35                  40                  45

Gly Lys Pro Phe Gln Leu Glu Ala Val Phe Glu Ala Asn Gln Asn Ser
 50                  55                  60

Lys Thr Ala Lys Ile Glu Ile Lys Ala Ser Ile Asp Gly Leu Glu Val
 65                  70                  75                  80

Asp Val Pro Gly Ile Asp Pro Asn Ala Cys His Tyr Met Lys Cys Pro
                 85                  90                  95

Leu Val Lys Gly Gln Gln Tyr Asp Ile Lys Tyr Thr Trp Asn Val Pro
                100                 105                 110

Lys Ile Ala Pro Lys Ser Glu Asn Val Val Thr Val Lys Val Met
            115                 120                 125

Gly Asp Asn Gly Val Leu Ala Cys Ala Ile Ala Thr His Ala Lys Ile
130                 135                 140

Arg Asp
145

<210> SEQ ID NO 2
<211> LENGTH: 438
<212> TYPE: DNA
<213> ORGANISM: Dermatophagoides pteronyssinus

<400> SEQUENCE: 2
atgatgtaca aaattttgtg tctttcattg ttggtcgcag ccgttgctgc tgatcaagtc      60
gatgtcaaag attgtgccaa tcatgaaatc aaaaagtttt ggtaccagg atgccatggt     120 tcagaatcat gtatcattca cgtggtaaa ccattccaat ggaagccgt tttcgaagcc      180 aaccaaaact caaaaccgc taaaattgaa atcaaagctt caatcgatgg tttagaagtt     240
gatgttcccg gtatcgatcc aaatgcatgc cattatatga atgtccatt ggttaaagga    300 caacaatatg atattaaata catggaatgt tccgaaaatt gcaccaaa atctgaaaat     360 gttgtcgtca ctgttaaagt tatgggtgat aatggtgttt tggcctgtgc tattgctact    420
catgctaaaa tccgcgat                                                   438

<210> SEQ ID NO 3
<211> LENGTH: 591
<212> TYPE: DNA
<213> ORGANISM: Dermatophagoides pteronyssinus

<400> SEQUENCE: 3
cacaaattct tctttcttcc ttactactga tcattaatct gaaaacaaaa ccaaacaaac      60
cattcaaaat gatgtacaaa attttgtgtc tttcattgtt ggtcgcagcc gttgctgctg     120
atcaagtcga tgtcaaagat tgtgccaatc atgaaatcaa aaagttttg gtaccaggat     180 gccatggttc agaatcatgt atcattcatc gtggtaaacc attccaattg aagccgttt     240 tcgaagccaa ccaaaactca aaaccgcta aaattgaaat caaagcttca atcgatggtt    300
tagaagttga tgttcccggt atcgatccaa atgcatgcca ttatatgaaa tgtccattgg    360
ttaaaggaca acaatatgat attaaatata catggaatgt tccgaaaatt gcaccaaaat    420
ctgaaaatgt tgtcgtcact gttaaagtta tgggtgataa tggtgttttg gcctgtgcta    480
ttgctactca tgctaaaatc cgcgattaaa ttcagcaaac aaacaaaatt tattgatttt    540
gtaatcaaat caattgattt tctttccaaa aaaataaaaa taagggaatt c             591
```

```
<210> SEQ ID NO 4
<211> LENGTH: 146
<212> TYPE: PRT
<213> ORGANISM: Dermatophagoides pteronyssinus

<400> SEQUENCE: 4

Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
            20                  25                  30

Val Leu Val Pro Gly Cys His Gly Ser Glu Pro Cys Ile Ile His Arg
        35                  40                  45

Gly Lys Pro Phe Gln Leu Glu Ala Val Phe Glu Ala Asn Gln Asn Thr
    50                  55                  60

Lys Thr Ala Lys Ile Glu Ile Lys Ala Ser Ile Asp Gly Leu Glu Val
65                  70                  75                  80

Asp Val Pro Gly Ile Asp Pro Asn Ala Cys His Tyr Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Val Met
        115                 120                 125

Gly Asp Asp Gly Val Leu Ala Cys Ala Ile Ala Thr His Ala Lys Ile
    130                 135                 140

Arg Asp
145

<210> SEQ ID NO 5
<211> LENGTH: 438
<212> TYPE: DNA
<213> ORGANISM: Dermatophagoides pteronyssinus

<400> SEQUENCE: 5
atgatgtaca aaattttgtg tctttcattg ttggtcgcag ccgttgctcg tgatcaagtc      60
gatgtcaaag attgtgccaa tcatgaaatc aaaaaagttt tggtaccagg atgccatggt     120
tcagaaccat gtatcattca cgtggtaaaa ccattccaat ggaagccgt ttttcgaagcc     180 aaccaaaaca caaaaacggc taaaattgaa atcaaagcct caatcgatgg tttagaagtt     240
gatgttcccg gtatcgatcc aaatgcatgc cattacatga atgcccatt ggttaaagga      300 caacaatatg atattaaata cacatggaat gttccgaaaa ttgcaccaaa atctgaaaat     360
gttgtcgtca ctgttaaagt tatgggtgat gatggtgttt tggcctgtgc tattgctact     420
catgctaaaa tccgcgat                                                   438

<210> SEQ ID NO 6
<211> LENGTH: 591
<212> TYPE: DNA
<213> ORGANISM: Dermatophagoides pteronyssinus

<400> SEQUENCE: 6
cacaaattct tctttcttcc ttactactga tcattaatct gaaaacaaaa ccaaacaaac      60
cattcaaaat gatgtacaaa attttgtgtc tttcattgtt ggtcgcagcc gttgctcgtg     120
atcaagtcga tgtcaaagat tgtgccaatc atgaaatcaa aaaagttttg gtaccaggat     180
gccatggttc agaaccatgt atcattcatc gtggtaaacc attccaattg aagccgttt     240 tcgaagccaa ccaaaacaca aaaacggcta aaattgaaat caaagcctca atcgatggtt     300
tagaagttga tgttcccggt atcgatccaa atgcatgcca ttacatgaaa tgcccattgg     360
```

-continued

```
ttaaaggaca acaatatgat attaaatata catggaatgt tccgaaaatt gcaccaaaat    420
ctgaaaatgt tgtcgtcact gttaaagtta tgggtgatga tggtgttttg gcctgtgcta    480
ttgctactca tgctaaaatc cgcgattaaa tcaaacaaaa tttattgatt ttgtaatcac    540
aaatgattga ttttctttcc aaaaaaaaaa taaataaaat tttgggaatt c            591

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gcggatccga tcaagtcgat gtcaaa                                          26

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
gcctcgagaa aagagatcaa gtcgatgtca aa                                   32

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
gcgaattctt aatcgcggat tttagc                                          26
```